United States Patent [19]
Wright

[11] Patent Number: 5,629,021
[45] Date of Patent: May 13, 1997

[54] MICELLAR NANOPARTICLES

[75] Inventor: D. Craig Wright, Gaithersburg, Md.

[73] Assignee: Novavax, Inc., Rockville, Md.

[21] Appl. No.: 380,942

[22] Filed: Jan. 31, 1995

[51] Int. Cl.$^6$ ..................................................... A61K 9/14
[52] U.S. Cl. ............................................ 424/489; 424/470
[58] Field of Search ............................. 514/3; 424/489, 424/470, 450; 252/312

[56] References Cited

U.S. PATENT DOCUMENTS

| | | | |
|---|---|---|---|
| 4,182,330 | 1/1980 | Michaels | 128/260 |
| 4,235,871 | 11/1980 | Papahadjopoulos et al. | 424/19 |
| 4,356,167 | 10/1982 | Kelly | 424/38 |
| 4,610,868 | 9/1986 | Fountain et al. | 424/1.1 |
| 4,725,442 | 2/1988 | Haynes | 424/490 |
| 4,744,989 | 5/1988 | Payne et al. | 424/490 |
| 4,824,675 | 4/1989 | Wong et al. | 424/438 |
| 5,120,710 | 6/1992 | Liedtke | 514/3 |
| 5,152,923 | 10/1992 | Weder et al. | 252/312 |

FOREIGN PATENT DOCUMENTS 2078543  1/1982  United Kingdom.

OTHER PUBLICATIONS

Rolland, A. et al. (1992) "New Macromolecular Carriers for Drugs. I. Preparation and Characterization of Poly (oxyethylene–b–isoprene–b–oxyethylene) Block Copolymer Aggregates" *Journal of Applied Polymer Science*, 44: 1195–1203.

*Primary Examiner*—Thurman K. Page
*Assistant Examiner*—William E. Benston, Jr.
*Attorney, Agent, or Firm*—Lahive & Cockfield

[57] ABSTRACT

The present invention relates to micellar nanoparticles and methods of their production. Micellar nanoparticles are made by hydrating a mixture of an oil, a stabilizer/surfactant, and an alcoholic initiator with an aqueous solution. These micellar nanoparticles are normally less than 100 nanometers in diameter. The micellar nanoparticles are particularly advantageous in delivering materials such as estradiol topically through the skin because their small size allows easy penetration.

12 Claims, 3 Drawing Sheets

MICELLAR NANOPARTICLES

BACKGROUND OF THE INVENTION

The present invention is concerned with the materials and methods for constructing "micellar nanoparticles," micelle-like particles with mean diameters less than 1000 nanometers (one micron). These micellar nanoparticles are submicron-sized, oil-based particles, the smallest of which are filterable through a 0.2 micron filter such as is standardly used for microbiological purification. The micellar nanoparticles of the invention may be formed into stable dispersions in aqueous solutions and buffers.

The micellar nanoparticles have a variety of uses because of their small size. Other synthetic particles such as liposomes, nonphospholipid lipid vesicles and microcapsules are normally a micron or larger. In contrast, it is possible to form the micellar nanoparticles of the invention in sizes less than 100 nanometers diameter. Unlike lipid vesicles, some of which can be engineered to carry an oil, see, e.g., U.S. Pat. No. 4,911,928 to Wallach, the present particles require at least an oil, a stabilizer/surfactant, an initiator, and water or another diluent in their manufacture. However, neither cholesterol nor phospholipids are used. In fact, these nanoparticles can be made using food grade, USP or NF grade materials suitable for human use applications. This is particularly important if these micellar nanoparticles are to be used for topical delivery of a material into the bloodstream. One specific use of this type of system is the delivery of natural or synthetic hormones such as estradiol. These materials often have solubility problems; e.g., they are often only soluble in materials such as ethanol which can be difficult to incorporate in stable particulate systems.

Micellar nanoparticles are unique in that they allow materials that are soluble in any of water, oil, or the initiator (i.e., ethanol or methanol) to be incorporated into stable particles with mean diameters between about 30 and 1000 nanometers. Most preparations have particle diameters between 30 to 500 nanometers, are mixable in water, and filterable through either 0.2 or 0.45 micron filters. They can be stored at between −20 and 25 degrees C°.

Utilizing the materials and methods describe, one can produce micellar nanoparticles that do the following:

1. Incorporate ethanol or methanol soluble drugs into the particles.
2. Incorporate ethanol or methanol soluble pesticides into the particles.
3. Incorporate adjuvants into the particles.
4. Incorporate proteins into the particles.
5. Incorporate whole viruses containing intact nucleic acids into the particles. It must be noted, however, that the smaller particles of the invention are about the same size as many viruses.
6. Incorporate ethanol-extracted flavors into the particles.
7. Incorporate volatile oils (flavors and fragrances) into the particles.
8. Incorporate a charge into the particles.
9. Create colored particles.

Of particular importance is the ability to transmit drugs topically. It has been known for many years that small particles, such as those below one micron in diameter, can more easily traverse the skin boundary than larger particles. However, the small amount of drug transmitted in small particles has often limited their usefulness In addition, most particles have only had limited classes of materials they could deliver.

Accordingly, an object of the invention is to produce submicron particles which can deliver a variety of classes of materials.

Another object of the invention is to produce submicron particles that can deliver materials that are soluble in ethanol or methanol but have limited or no solubility in aqueous and oil systems.

A further object of the invention is to produce particles below 100 nanometers in diameter that can be used for drug delivery.

A still further object of the invention is to produce a particle for topical delivery of hormones such as estradiol.

These and other objects and features of the invention will be apparent from the description and the claims.

SUMMARY OF THE INVENTION

The present invention features micellar nanoparticles and methods of their manufacture. These micellar nanoparticles have particular utility as drug delivery vehicles, with specific applications to topical delivery of materials that are soluble in ethanol and methanol. However, these micellar nanoparticles can also be used to deliver many different classes of drugs and other materials. The small size of the micellar nanoparticles and their compatibility with tissue render them applicable to numerous uses.

The micellar nanoparticles of the invention have diameters of about 10–1000 nanometers, with most of the particles having diameters of under 100 nanometers. This small particle size allows passage through a 0.2 micron filter. The nanoparticles are made of a lipophilic phase which includes an oil, a stabilizer (or surfactant) and an initiator such as ethanol or methanol. This lipophilic phase is hydrated by an aqueous solution such as water or a buffer. Preferred stabilizers are non-phospholipid surfactants, particularly the Tween (polyoxyethylene derivatives of sorbitan fatty acid esters) family of surfactants and the nonylphenol polyethylene glycol ethers. Most preferred surfactants are Tween 60 (polyoxyethylene 20 sorbitan monostearate) and Tween 80 (polyoxyethylene 20 sorbitan monooleate), and Tergitol NP-40 (Poly(oxy-1,2-ethanediyl), α-(4-nonylphenol)-ω-hydroxy, branched [molecular weight average 1980]) and Tergitol NP-70 (a mixed surfactant—AQ=70%). The high molecular weight of these surfactants appears to have advantageous properties in manufacture and stability of the resulting micellar nanoparticles.

The preferred initiators in the present invention are ethanol and methanol, but other short chain alcohols and or amides may be used in certain circumstances. While pure ethanol or methanol are preferred, mixtures of the two, and materials, blended or unblended, containing at least 50% alcohol, can be used. This group of initiators can include flavored initiators such as alcoholic extracts of flavors like peppermint, lemon, orange and the like.

In addition to the initiator and the surfactant of stabilizer, the micellar particles can be modified or custom manufactured by selection of the proper oil. While most oils seem to work, the preferred oils are selected from the group consisting of vegetable oils, nut oils, fish oils, lard oil, mineral oils, squalane, tricaprylin, and mixtures thereof.

A number of other materials may be added to the micellar nanoparticles to customize the particles. Volatile oils, such as volatile flavor oils, can be used in lieu of some the oil or can be added in addition to the other oil forming the particles. A coloring agent, such as a food coloring agent can also be used, preferably by adding it to the initiator. The initiator or the oil can also carry actives which are incorporated into the final particle suspension. These actives can be dissolved, or suspended in the liquid. One preferred additive is a steroid or hormone such as estradiol, which can be dissolved in an ethanol initiator and incorporated into the particle. Since estradiol precipitates in aqueous solutions, the addition of the aqueous phase will precipitate the estradiol, which can then be released in a topical preparation. One interesting fact that appears is that the type of crystals formed using the methods of the present invention are different in shape than standard aqueous solution precipitates of estradiol.

The aqueous solution which is used to hydrate the lipophilic phase is preferably a physiologically compatible solution such as water or a buffer, e.g., phosphate buffered saline. The aqueous solution may have an active material dissolved or suspended therein for incorporation. The basic procedure for the manufacture of the micellar nanoparticles is blending the oil, the stabilizer/surfactant, and the initiator to form a lipophilic phase and blending an excess, preferably about a 4:1 ratio, of the lipophilic phase with an aqueous dilulent solution. The blending, or hydrating, of the lipophilic phase with the aqueous phase is preferably accomplished using a device which generates a relative velocity of about 50 m/s through an orifice diameter of 1/18,000 of an inch. This shear provides particles in the preferred size range while lower shear values, e.g., by using larger orifices or lower velocities, can cause larger particle size.

All of the different materials and processes described herein can be modified or selected to control the properties of the resulting micellar nanoparticles. Actives can be carried in the oil, the initiator, or the aqueous phase for incorporation into the particles. Although it appears that the particles are micelles, they may be in the form of reverse micelles without changing the scope of the invention. The invention is further illustrated by the following detailed description and the drawing.

DETAILED DESCRIPTION OF THE INVENTION

Figure 1A:
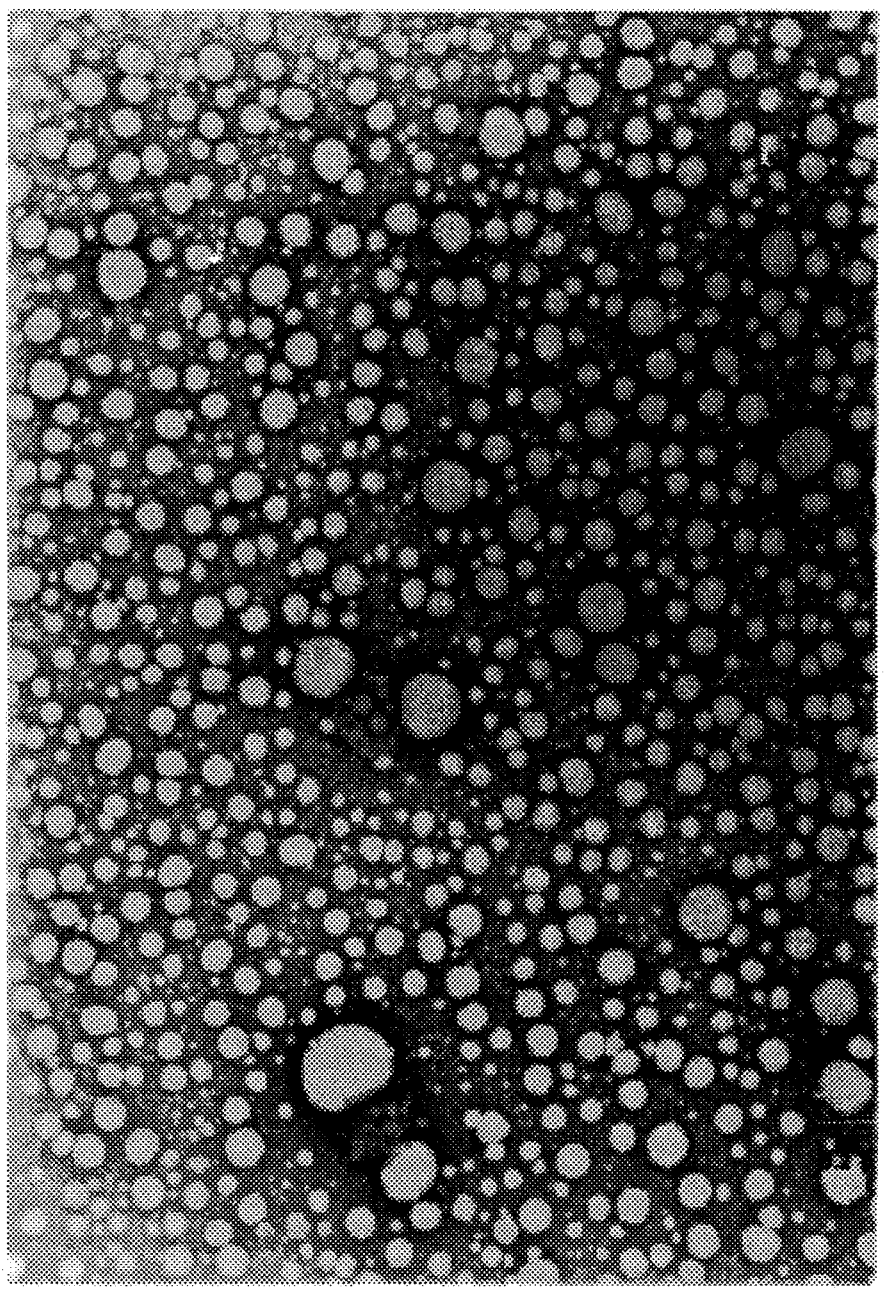
FIG. 1a and 1b are electromicrographs of the nanoparticles of the invention at two different magnifications.

The present invention concerns micellar nanoparticles and methods of their production. Unlike microcapsules and liposomal systems, the present micellar nanoparticles have a significant size population under 100 nanometers in diameter, while still carrying significant quantities of active ingredients. These micellar nanoparticles are particularly useful as topical drug delivery vehicles because their small size and other characteristics which permit rapid dermal penetration. The micellar nanoparticles are also exceptionally versatile in that the active materials which can be carried include those which are suspendable or dissolvable in any of the oil, aqueous dilulent, or, preferable, the initiator. These properties allow this system to be used with actives that are difficult to use in other delivery systems.

Micellar nanoparticles are formed by first combining at least one oil, preferably an oil selected from Table 1, a stabilizer (surfactant), preferably a surfactant from Table 2, and an initiator, preferably ethanol or methanol. Most preferred stabilizers are Tween 60, Tween 80, Tergitol NP-40 and Tergitol NP-70. Additional possible initiators are shown in Table 3 (alcohols and related compounds) and Table 4 (alcohol flavored extracts). If any of the alcohol flavored extracts of Table 4 are used which are less than 50% ethanol, a 1:1 mixture of ethanol and the extract is used to ensure that at least 50% ethanol is used. Volatile oils can also be added to these chemical components (Table 5), and colors may also be added to the oil-stabilizer-initiator mixture (Table 6). A negative charge may be introduced by addition of oleic acid to the oil-stabilizer-initiator mixture. After pre-mixing these materials, water or a suitable buffer such as those shown in Table 7 is injected under a high velocity into this mixture. The preferred ratio of oil:stabilizer:initiator is 25:3:5, respectively, on a volume per volume basis. The preferred ratio of the pre-mixed oil containing phase to water is 4:1, respectively. Nanoparticles can be produced with reciprocating syringe instrumentation, continuous flow instrumentation, or high speed mixing equipment. Particles created at this 4:1 ratio range in diameters from 30 to 500 nanometers. These water miscible particles can then be filtered through either a 0.2 or 0.45 micron filter. Larger micellar particles can be created by simply increasing the water content, decreasing the oil-stabilizer-initiator content, or changing the shear in forming the particles. We have coined the name "micellar nanoparticles" for particles with mean diameters less than 1000 nanometers (one micron).

TABLE 1

| Oils Utilized in Preparation of Micellar Nanoparticles. |
|---|
| Almond oil, sweet |
| Apricot seed oil |
| Borage oil |
| Canola oil |
| Coconut oil |
| Corn oil |
| Cotton seed oil |
| Fish oil |
| Jojoba bean oil |
| Lard oil |
| Linseed oil, boiled |
| Macadamia nut oil |
| Mineral oil |
| Olive oil |
| Peanut oil |
| Safflower oil |
| Sesame oil |
| Soybean oil |
| Squalane |
| Sunflower seed oil |
| Tricaprylin (1,2,3 trioctanoyl glycerol) |
| Wheat germ oil |

TABLE 2

| Stabilizers/Surfactants Utilized in Preparation of Micellar Nanoparticles. |
|---|
| Tween 60 |
| Tween 80 |
| Nonylphenol Polyethylene Glycol Ethers (alkylphenol-hydroxypolyoxyethylene) |
| 1. Poly(oxy-1,2-ethanediyl), alpha-(4-nonylphenol)-omega-hydroxy-, branched (i.e. Tergitol NP-40 Surfactant) Formula: $C_{95}H_{185}O_{40}$ MW (average) = 1980 |
| 2. Nonylphenol Polyethylene Glycol Ether mixtures (i.e. Tergitol NP-70 (70% AQ) Surfactant] Formula and MV: not applicable (mixture) |

TABLE 3

Initiators Utilized in Preparation of Micellar Nanoparticles.

Ethanol
Methanol

TABLE 4

Flavored Initiators (flavored extracts*)
Utilized in Preparation of Micellar Nanoparticles.

| | |
|---|---|
| Pure Anise extract | (73% Ethanol) |
| Imitation Banana extract | (40% Ethanol) |
| Imitation Cherry extract | (24% Ethanol) |
| Chocolate extract | (23% Ethanol) |
| Pure Lemon extract | (84% Ethanol) |
| Pure Orange extract | (80% Ethanol) |
| Pure Peppermint extract | (89% Ethanol) |
| Imitation Pineapple extract | (42% Ethanol) |
| Imitation Rum extract | (35% Ethanol) |
| Imitation Strawberry extract | (30% Ethanol) |
| Pure Vanilla extract | (35% Ethanol) |

*Extracts utilized are food grade materials (McCormick). Materials from other sources could be substituted.

TABLE 5

Volatile Oils or Fragrances Utilized in Preparation of Micellar Nanoparticles.

Balm oil
Bay oil
Bergamot oil
Cedarwood oil
Cherry oil
Cinnamon oil
Clove oil
Origanum oil
Peppermint oil

TABLE 6

Food Colors* Utilized in Preparation of Micellar Nanoparticles.

Green
Yellow
Red
Blue

*Food colors utilized are food grade materials (McCormick). Materials from other sources could be substituted.

TABLE 7

List of Diluents Utilized in Preparation of Micellar Nanoparticles.

Water for injection
Phosphate buffered saline

The following Examples will more clearly illustrate the invention and its usefulness.

EXAMPLE 1

Production of Uncharged Micellar Nanoparticles

Table 8 contains the materials used to produce micellar nanoparticles where water is the diluent. Sizing parameters using a Coulter L 130 Laser sizing apparatus are shown in Table 9.

TABLE 8

Preparation of Micellar nanoparticles utilizing water as the diluent.

| Chemical Component | Amount |
|---|---|
| Soybean oil (Oil) | 25 mL |
| Polysorbate 80 (Tween 80) (Stabilizer) | 3 mL |
| Ethanol (Initiator) | 5 mL |

Figure 1B:
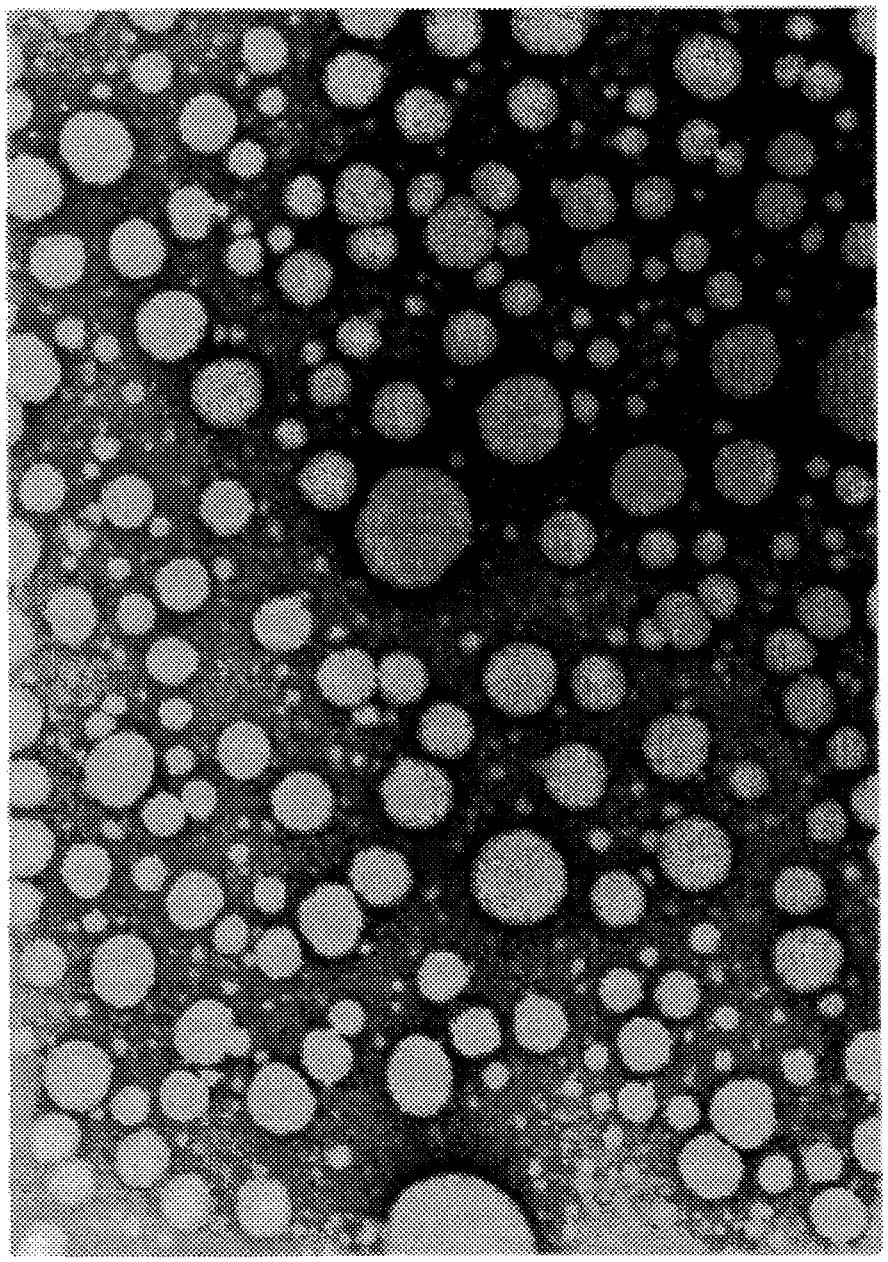

The above Oil-Stabilizer-Initiator components are mixed for 60 seconds. One mL of water is injected into four mL of the mixture using reciprocating syringe instrumentation. This instrumentation has two 5mL syringes connected together through a stainless steel Leurlok connector with a 1/18,000 inch orifice. The solutions are driven between the syringes, through the connector, for about 100 seconds. The resulting particles were dried on EM grids, stained with uranyl acetate, and electron micrograph studies performed. FIG. 1a shows an electromicrograph of this preparation at a 60,000X magnification while FIG. 1b shows the same preparation at a 150,000X magnification. A brief description of the method of production of the micellar nanoparticles follows each table.

TABLE 9

Sizing of Micellar Nanoparticles using water as a Diluent

| Preparation | LS-130 Mean Diameter (nanometers) | LS-130 Range (nanometers) |
|---|---|---|
| Micellar nanoparticles (SBO/Tw80/E/WFI) | 312 | 193–455 |

One problem with using the LS 130 sizing device is that it cannot accurately size particles which are less than 200 nanometers in diameter. Using FIGS. 1a and 1b, it is determined that most of the particles are between 70 and 90 nanometers in diameter, with only 5% of particles be greater than 90 nanometers in diameter. Particles in the range of 20–30 nanometers are visible in the higher magnification shown in FIG. 1b.

EXAMPLE 2

Incorporation of Estradiol into Micellar Nanoparticles

Tables 10 and 12 contain the materials utilized to produce two lots of uncharged micellar nanoparticles into which estradiol has been incorporated at two different concentrations. Both preparations are made using water as the diluent. The higher estradiol concentration materials were used in the rhesus monkey studies described in Example 3 below. Either 50 or 100 mg of estradiol is solublized in the initiator (ethanol component) of the preparation prior to formation of the micellar nanoparticles. This is necessary since estradiol precipitates in the presence of water. In fact, the small amount of water in the reagent grade ethanol appears to be sufficient to precipitate the estradiol since the micellar particles formed using the materials and procedures described herein appear to have crystals of estradiol contained therein. However, these crystals appear to have a sheet-like form rather than the needle-like form standardly found in water precipitation.

TABLE 10

Preparation of Micellar Nanoparticles Containing Estradiol

| Chemical Component | Amount |
| --- | --- |
| Soybean oil (Oil) | 25 mL |
| Polysorbate 80 (Tween 80) (Stabilizer) | 3 mL |
| Ethanol (Initiator) | 5 mL |
| Estradiol | 50 mg |

The micellar nanoparticles were made using procedures substantially identical to that described in Example 1, except the estradiol was dissolved (or suspended) in the ethanol initiator prior to the mixing of the initiator with the other components. The oil-stabilizer-initiator/estradiol components are hand mixed or can be mixed for 60 seconds using a vortex mixer. One mL of water is injected into four mL of the resulting mixture using reciprocating syringe instrumentation such as is described in Example 1.

TABLE 11

Sizing data on Estradiol containing Micellar Nanoparticles (50 mg)

| Preparation | LS-130 Mean Diameter (nanometers) | LS-130 Range (nanometers) |
| --- | --- | --- |
| Micellar nanoparticles (SBO/Tw80/Etoh-estradiol/WFI) | 289 | 174–459 |

Sizing data on these preparations, measured using a Coulter LS130 Laser sizing apparatus, is shown in Tables 11 and 13, respectively, for the two preparations. The LS130 sizing device cannot size particles accurately less than 200 nanometers in diameter. These materials were also dried on EM grids, stained with uranyl acetate and electron micrograph studies performed. Electron micrographs reveal that most of the particles are less than 200 nanometers. Particles in the range of 20–30 nanometers are visible. Crystallized estradiol is readily visible in the larger micelles. No free drug crystals are noted in any fields suggesting complete incorporation of drug into micelles.

TABLE 12

Preparation of Micellar Nanoparticles Containing Estradiol

| Chemical Component | Amount |
| --- | --- |
| Soybean oil (Oil) | 25 mL |
| Polysorbate 80 (Tween 90) (Stabilizer) | 3 mL |
| Ethanol (Initiator) | 5 mL |
| Estradiol | 100 mg |

TABLE 13

Sizing data on Estradiol containing Micellar Nanoparticles (100 mg)

| Preparation | LS-130 Mean Diameter (nanometers) | LS-130 Range (nanometers) |
| --- | --- | --- |
| Micellar nanoparticles (SBO/Tw80/Etoh-estradiol/WFI) | 217 | 151–291 |

EXAMPLE 3

Rhesus Monkey Testing of Estradiol Containing Preparations

The 100 mg estradiol preparation of Example two was tested against a standard ethanol preparation of estradiol to show efficacy. One milligram of estradiol, in either ethanol (Table 14) or micellar nanoparticles (Table 15), was applied to the skin of groups of four ovariectomized rhesus monkeys. Serial blood samples were drawn and serum estradiol levels were determined over the next 32 days. The serum estradiol data is graphically depicted in FIG. 2. No additional drug was applied to skin of any animal. Animals were observed for the next 60 days to determine whether the time of occurrence, duration and severity of vaginal bleeding (Table 16).

TABLE 14

Serum Estradiol Levels in Ovariectomized Female Monkeys Following a Single Topical Application of Micellar Nanoparticles Equivalent to 1 mg Estradiol

| Sample Time | Monkey Number Serum Estradiol | | | | |
|---|---|---|---|---|---|
| | #19567 (pg/ml) | #21792 (pg/ml) | #22366 (pg/ml) | #22405 (pg/ml) | Group Mean ± S.E. |
| 0 hour | 0.0[b] | 0.0[b] | 0.0[b] | 0.0[b] | 0.0 ± 0.0[b] |
| 0.5 hour | 22.2 | 49.8 | 36.9 | 77.5 | 46.6 ± 11.7 |
| 1 hour | 37.4 | 60.9 | 65.6 | 108.6 | 68.1 ± 14.8 |
| 2 hours | 61.5 | 80.5 | 87.3 | 191.3 | 105.2 ± 29.2 |
| 4 hours | 77.2 | 132.1 | 120.6 | 120.4 | 112.6 ± 12.1 |
| 6 hours | 89.0 | 166.3 | 119.0 | 158.3 | 133.2 ± 18.0 |
| 8 hours | 87.5 | 157.3 | 116.1 | 148.1 | 127.3 ± 15.9 |
| 12 hours | 83.0 | 160.5 | 100.6 | 140.3 | 121.1 ± 17.8 |
| day 1 | 90.7 | 178.0 | 105.7 | 132.6 | 126.8 ± 19.2 |
| day 2 | 95.5 | 152.8 | 90.6 | 83.5 | 105.6 ± 15.9 |
| day 3 | 81.9 | 122.6 | 51.1 | 47.2 | 75.7 ± 17.5 |
| day 4 | 91.5 | 83.9 | 58.7 | 50.3 | 71.1 ± 9.9 |
| day 5 | 41.6 | 74.7 | 35.1 | 40.0 | 47.9 ± 9.1 |
| day 6 | 45.2 | 63.7 | 25.6 | 40.9 | 43.9 ± 7.8 |
| day 7 | 18.3 | 25.9 | 21.9 | 27.0 | 23.3 ± 2.0 |
| day 12 | 0.0[b] | 0.0[b] | 0.0[b] | 0.0[b] | 0.0 ± 0.0[b] |
| day 17 | 0.0[b] | 0.0[b] | 0.0[b] | 0.0[b] | 0.0 ± 0.0[b] |
| day 22 | 0.0[b] | 0.0[b] | 0.0[b] | 0.0[b] | 0.0 ± 0.0[b] |
| day 27 | 0.0[b] | 0.0[b] | 0.0[b] | 0.0[b] | 0.0 ± 0.0[b] |
| day 32 | 0.0[b] | 0.0[b] | 0.0[b] | 0.0[b] | 0.0 ± 0.0[b] |

[a]CDB 3988 = 2.4 mg estradiol/ml of Tween/Oil. The dosing volume was 0.42 ml.
[b]0 = Not Detectable. The limit of detection ($ED_{90}$) for the assay was 13.3 ± 2.4 pg/ml (mean ± S.E., n = 4)

TABLE 15

Serum Estradiol Levels in Ovariectomized Female Monkeys Following a Single Topical Application of 1 mg Ethanol Containing Estradiol[a]

| Sample Time | Monkey Number Serum Estradiol | | | | |
|---|---|---|---|---|---|
| | #G-558 (pg/ml) | #G-603 (pg/ml) | #E-920 (pg/ml) | #E-924 (pg/ml) | Group Mean ± S.E. |
| 0 hour | 0.0[b] | 0.0[b] | 0.0[b] | 0.0[b] | 0.0 ± 0.0[b] |
| 0.5 hour | 17.7 | 97.1 | 44.8 | 19.5 | 44.8 ± 18.5 |
| 1 hour | 53.2 | 44.1 | 88.3 | 99.9 | 71.4 ± 13.5 |
| 2 hours | 144.3 | 89.4 | 138.5 | 155.1 | 131.8 ± 14.6 |
| 4 hours | 143.7 | 202.3 | 165.1 | 193.6 | 176.2 ± 13.4 |
| 6 hours | 155.8 | 257.8 | 173.1 | 203.7 | 197.6 ± 22.4 |
| 8 hours | 114.2 | 266.1 | 130.7 | 130.0 | 160.3 ± 35.5 |
| 12 hours | 80.8 | 219.5 | 86.4 | 115.9 | 125.7 ± 32.2 |
| day 1 | 92.4 | 145.2 | 56.9 | 109.4 | 101.0 ± 18.4 |
| day 2 | 74.1 | 124.2 | 55.3 | 107.2 | 90.2 ± 15.6 |
| day 3 | 65.0 | 67.4 | 51.9 | 89.2 | 68.4 ± 7.7 |
| day 4 | 70.5 | 79.6 | 57.8 | 90.0 | 74.5 ± 6.8 |
| day 5 | 53.6 | 53.2 | 51.6 | 47.3 | 51.4 ± 1.4 |
| day 6 | 60.1 | 59.0 | 59.4 | 53.0 | 57.9 ± 1.6 |
| day 7 | 48.7 | 40.6 | 50.3 | 36.6 | 44.1 ± 3.3 |
| day 12 | 28.5 | 24.2 | 53.3 | 0.0[b] | 26.4 ± 10.9[b] |
| day 17 | 0.0[b] | 0.0[b] | 28.9 | 0.0[b] | 7.2 ± 7.2[b] |
| day 22 | 0.0[b] | 0.0[b] | 13.8 | 0.0[b] | 3.5 ± 3.5 |
| day 27 | 0.0[b] | 0.0[b] | 0.0[b] | 0.0[b] | 0.0 ± 0.0[b] |
| day 32 | 0.0[b] | 0.0[b] | 0.0[b] | 0.0[b] | 0.0 ± 0.0[b] |

[a]CDB 100 = 2.4 mg estradiol/ml of absolute ethanol. The dosing volume was 0.42 ml.
[b]0 = Not Detectable. The limit of detection ($ED_{90}$) for the assay was 13.3 ± 2.4 pg/ml (mean ± S.E., n = 4)

Figure 2:
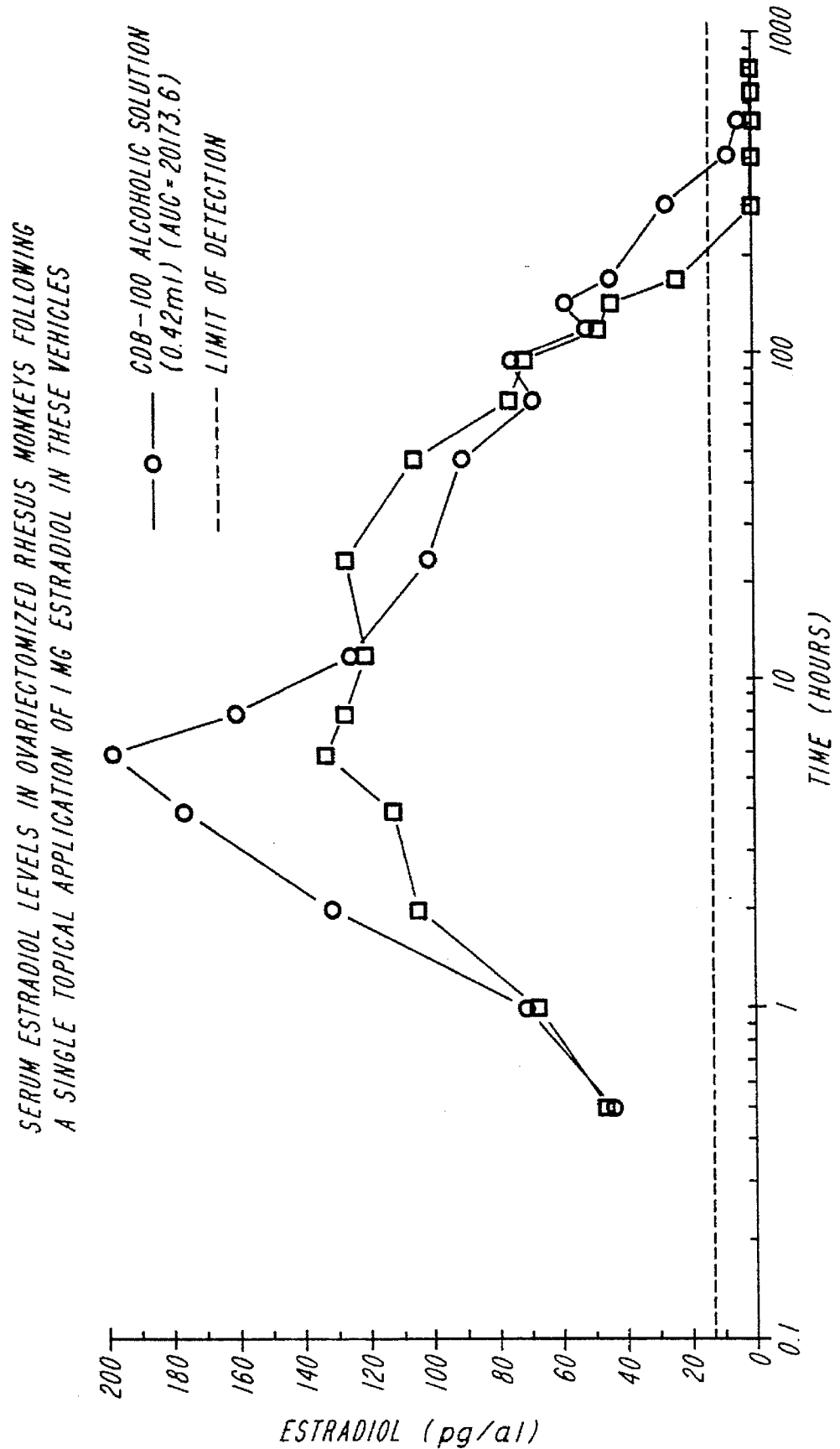
FIG. 2 is a graph of serum estradiol levels in ovariectomized Rhesus monkeys following topical administration of 1 mg of estradiol using three different types of vehicles.

The data in Tables 14 and 15 and FIG. 2 show that therapeutic serum levels of estrogen are present in the blood stream of ovariectomized animals in both groups in one hour after a single application. Mean estradiol levels greater than 40 picograms/ml are maintained for 7 days with the ethanol preparation and for 6 days with the nanoparticle preparation. When estrogen levels remain low (see FIG. 2 and Table 16), vaginal bleeding occurs in both groups. Also of particular interest is the shape of the curves in FIG. 2. The ethanol-estradiol preparation yields a "shark tooth" curve showing a high initial action and a sharp fall-off while the micellar nanoparticle preparation yields more of a "mesa" effect with a nearly flat level for several hours. This "mesa" effect is often preferred since some of the problems associated with peaking can be minimized.

TABLE 16

ESTROGEN WITHDRAWAL BLEEDING IN OVARIECTOMIZED RHESUS MONKEYS FOLLOWING A SINGLE TOPICAL APPLICATION OF ESTRADIOL IN ALCOHOL OR MICELLAR NANOPARTICLES

| | | WITHDRAWAL BLEEDING | | |
| | | DAYS | | |
| CDB No. | ESTRADIOL ESTER | LATENCY | DURATION | INTENSITY[a] |
| --- | --- | --- | --- | --- |
| 100 | Estradiol in alcoholic solution | 19.5 ± 0.3 | 4.3 ± 0.9 | 1.6 ± 0.2 |
| 3988 | Estradiol formulation[b] | 16.5 ± 0.5[c] | 7.3 ± 1.5 | 1.6 ± 0.1 |

[a]Mean intensity of bleeding (1 = scant, moderate, 3 = heavy) over bleeding period
[b]Novavax MN Suspension 11294-2
[c]Significantly different ($p < 0.01$) from estradiol in alcohol solution based on a one-way analysis of variance followed by a Student Neuman-Keuls multiple range test Therefore, this Example demonstrates in a non-human primate that the micellar nanoparticles of the invention can be utilized to deliver estradiol through intact skin with maintenance of therapeutic serum estradiol levels for 6 days after a single application. This technology may have numerous therapeutic applications in medicine.

The estadiol preparation is also stable at a variety of temperatures. Table 17 shows thermal stability data for the micellar nanoparticle preparation of the Example 2 at −20° C., 25° C., and 65° C. As is clear, while the micellar nanoparticles are unstable at high temperatures, they are stable at room temperature and low temperatures.

TABLE 17

Thermal Stability of Micellar Nanoparticles

| Preparation | LS-130 Mean Diameter (nanometers) | LS-130 Range (nanometers) |
| --- | --- | --- |
| Micellar nanoparticles (SBO/Tw80/Etoh-estradiol/WFI) Storage at 25° C. | 361 | 168–599 |
| Micellar nanoparticles (SBO/Tw80/Etoh-estradiol/WFI) Storage at −20° C. | 312 | 179–510 |
| Micellar nanoparticles (SBO/Tw80/Etoh-estradiol/WFI) Storage at 65° C. | Unstable | |

In addition, the micellar nanoparticles of the invention can be diluted with aqueous solutions without stability loss. This allows the possibility of using high concentration products which can be diluted for use as necessary.

Those skilled in the art will recognize, or be able to ascertain using no more than routine experimentation, many equivalents to the specific embodiments of the invention described herein. Such equivalents are intended to be encompassed by the following claims.

What is claimed is:

1. A micellar nanoparticle having a diameter of between about 25 and 1000 nm, said micellar nanoparticle comprising a lipophilic phase which includes an oil, a stabilizer and an alcohol-based initiator, hydrated with a suitable aqueous solution wherein said stabilizer is selected from the group consisting of Tween 60, Tween 80, nonylphenol polyethylene glycol ethers, and mixtures thereof.

2. The micellar nanoparticle of claim 1 wherein said initiator is selected from the group consisting of alcoholic materials containing methanol, ethanol and mixtures thereof.

3. The micellar nanoparticle of claim 2 wherein said initiator is selected from the group consisting of alcoholic materials containing 50% or higher ethanol, methanol, and mixtures thereof.

4. The micellar nanoparticle of claim 1 wherein said oil is selected from the group consisting vegetable oils, nut oils, fish oils, lard oil, mineral oils, squalane, tricaprylin, and mixtures thereof.

5. The micellar nanoparticle of claim 1 wherein said aqueous solution comprises a physiologically compatible solution.

6. The micellar nanoparticle of claim 1 wherein said aqueous solution is selected from the group consisting of water, and phosphate buffered saline.

7. The micellar nanoparticle of claim 1 wherein said aqueous phase has an active material dissolved or suspended therein.

8. The micellar nanoparticle of claim 1 wherein said oil has an active material dissolved or suspended therein.

9. The micellar nanoparticle of claim 1 wherein said initiator has an active material dissolved or suspended therein.

10. The micellar nanoparticle of claim 9 wherein said active material comprises estradiol.

11. The micellar nanoparticle of claim 1 wherein said micellar nanoparticle is dispersible in aqueous solution.

12. The micellar nanoparticle of claim 1 wherein the diameter of said micellar nanoparticle allows passage through a 0.2 mm filter.

* * * * *